(12) United States Patent
Murayama et al.

(10) Patent No.: US 6,486,333 B1
(45) Date of Patent: Nov. 26, 2002

(54) FUNCTIONAL ALCOHOL RELEASING SUBSTANCE

(75) Inventors: Koichi Murayama; Shigeyoshi Tanaka, both of Wakayama; Atsushi Katayama, Tokyo; Ryoichi Hirayama, Tokyo; Takami Gema, Tokyo, all of (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/708,632

(22) Filed: Nov. 9, 2000

(30) Foreign Application Priority Data

Nov. 10, 1999 (JP) .............................. 11-319395

(51) Int. Cl.⁷ ............................................ C07C 233/00
(52) U.S. Cl. ...................................................... 554/52
(58) Field of Search ............................................ 554/52

(56) References Cited

U.S. PATENT DOCUMENTS 5,958,870 A    9/1999  Declercq et al.

FOREIGN PATENT DOCUMENTS

WO    WO 96/38528    12/1996

OTHER PUBLICATIONS

Chem. Abstr., 105:190468, 1986.*

* cited by examiner

*Primary Examiner*—Deborah D. Carr
(74) *Attorney, Agent, or Firm*—Oblon, Spivak, McClelland, Maier & Neustadt, P.C.

(57) ABSTRACT

This invention discloses a substance which is a betaine ester of a functional alcohol that has an amido bond in its molecule and releases the functional alcohol.

5 Claims, No Drawings

FUNCTIONAL ALCOHOL RELEASING SUBSTANCE

BACKGROUND OF THE INVENTION

1. Field of the Invention

This invention relates to a functional alcohol releasing substance which gradually releases a functional alcohol and to a composition such as of a detergent or softening agent, which contains the functional alcohol releasing substance.

2. Description of the Related Art

In a fragrance, a desired aroma is created by blending a large number of aromatic components so-called top note, middle note and base note having different volatility. During the use of the fragrance, components having higher volatility vaporize in priority and, as a result, the aroma of the fragrance changes with the lapse of time, thus posing a problem in that the aroma cannot be maintained constantly for a prolonged period of time. A gel-like aromatic composition in which a fragrance is included in microcapsules and dispersed in a gel base material is known as a means for solving such a problem (JP-A-63-260567; the term"JP-A" as used herein means an "unexamined published Japanese patent application"). Though this method is effective in gel-like preparations, the desired effect cannot be obtained in the case of liquid preparations having low viscosity due to generation of floating and precipitation of microcapsules.

In addition to the above, a precursor of fragrance raw material in which a sugar and an amino acid are added to a fragrance raw material and a technique for gradually releasing the fragrance raw material by allowing an enzyme to act upon the precursor have been disclosed (JP-A-4-170961). This method, however, has problems in that its effect in the actual use system varies depending on the presence or absence of the hydrolyzing enzyme and, when the precursor and hydrolyzing enzyme are simultaneously blended in a product system, hydrolysis progresses in the product. It also poses the same problems in volatile antibacterial and antifungal agents, so that it is difficult to maintain their effects. In addition, even a nonvolatile substance, e.g. in the case of a water-soluble substance, cannot maintain its effect due to its washing with water.

On the other hand, WO 96/38528 discloses a betaine ester quaternary ammonium salt derivative which can gradually release a fragrance raw material alcohol. However, this betaine ester quaternary ammonium salt is apt to cause side reactions at the time of synthesis and has a considerably high hydrolyzing rate even in a neutral to weakly acidic aqueous solution, so that it has a disadvantage of poor blending stability.

SUMMARY OF THE INVENTION

An object of the invention is to provide a functional substance releasing compound which can be stably blended independent of the form and use of preparations and can gradually release a functional substance constantly for a prolonged period of time in an actual use system.

The invention is a substance which is a betaine ester of a functional alcohol, in which it has an amido bond in its molecule and releases the functional alcohol, and a composition containing the same.

The term betaine ester as used herein means a structure in which a free acid as the hydration product of betaine and an alcohol are esterificated.

DETAILED DESCRIPTION OF THE INVENTION

As the functional alcohol releasing substance of the invention, a compound represented by a general formula (I) (to be referred to as betaine ester (I) hereinafter) can be exemplified:

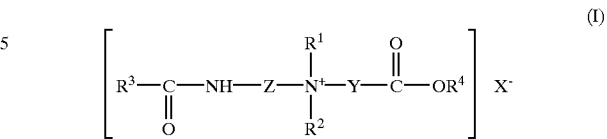

wherein each of $R^1$, $R^2$ and $R^3$ independently represents hydrogen atom or a straight- or branched-chain alkyl or alkenyl group having from 1 to 30 carbon atoms, Y represents a straight- or branched-chain alkylene group having from 1 to 4 carbon atoms, Z is a group represented by —$R^5$(OA) n— (wherein $R^5$ is a straight- or branched-chain alkylene group having from 1 to 30 carbon atoms, and A is a straight- or branched-chain alkylene group having from 2 to 4 carbon atoms, and n is a number of from 0 to 10), $R^4$ represents a residue in which one OH is removed from a functional alcohol having at least one hydroxyl group in its molecule, illustratively, $R^4$ represents a saturated or unsaturated aliphatic hydrocarbon group or aromatic hydrocarbon group having from 1 to 11 carbon atoms, or an alkadienyl group, alkatrienyl group, aryl group, arylalkyl group or monocyclic, bicyclic or tricyclic terpene hydrocarbon group, each having from 12 to 30 carbon atoms, wherein a part of the hydrogen atoms on the hydrocarbon group of $R^4$ may be substituted by a halogen atom or hydroxyl group, the methylene group in the hydrocarbon group of $R^4$ may be substituted by carbonyl group, amido bond, oxygen atom or sulfur atom, the methyl group may be substituted by formyl group or —$CONH_2$, the carbon-carbon double bond may be substituted by epoxy group and, when isomers are present in $R^4$, it may be a mixture of isomers, and $X^-$ represents an anion.

In this case, the alkyl group, alkenyl group and alkylene group may have a substituent group, and examples of the substituent group include an aryl group such as phenyl group, an alkoxy group such as methoxy group or ethoxy group and an aryloxy group such as phenoxy group.

The betaine ester (I) can be obtained for example by allowing a compound represented by a general formula (III) (to be referred to as compound (III) hereinafter) to react with a compound represented by a general formula (IV) (to be referred to as compound (IV) hereinafter) in the presence of a solvent:

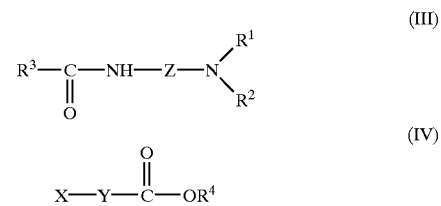

wherein $R^1$, $R^2$, $R^3$, $R^4$, X, Y and Z are as defined in the foregoing.

Examples of the solvent to be used include diethyl ether, acetone and chloroform which are selected in response to the solubility of each material. The reaction temperature can be selected within the range of from 15 to 100° C. depending on the boiling point of the solvent used and is preferably from 25 to 50° C., more preferably from 40 to 45° C. Regarding the blending ratio of the compound (III) and compound (IV), it is desirable to use excess amount of the compound (IV) in order to increase the reaction ratio and facilitate purification of the product, and it is preferably within the range of from 1:1 to 1:1.2 by molar ratio for practical purpose.

The compound (III), when the number of carbons of the acyl group represented by $R^3CO-$ is 8 or more, can be quantitatively obtained by heat-melting the corresponding fatty acid at 160 to 180° C. in an atmosphere of nitrogen and slowly adding a compound represented by a general formula (V) dropwise thereto, thereby effecting dehydration condensation. Also, when the number of carbons of the acyl group represented by $R^3CO-$ is less than 8, it can be obtained by allowing an acid anhydride or acid chloride of the corresponding fatty acid to react with the compound of general formula (V).

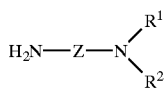
(V)

In this formula, $R^1$, $R^2$ and Z are as defined in the foregoing.

The compound (IV) can be obtained by condensing a compound represented by a general formula (VI) with an alcohol represented by a general formula (VII) in the presence of amine as a base.

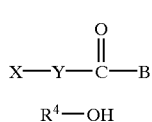

In the above formulae, $R^4$, X and Y are as defined in the foregoing, and B represents a halogen atom.

Among compounds of the betaine ester (I), particularly preferred is a compound represented by a general formula (II) (to be referred to as betaine ester (II) hereinafter).

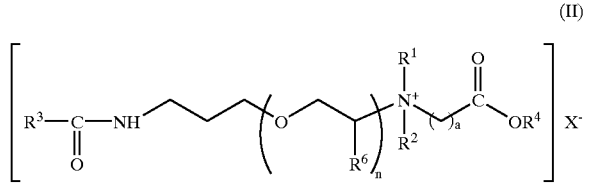
(II)

In this formula, $R^1$, $R^2$, $R^3$, $R^4$, n and $X^-$ are as defined in the foregoing, $R^6$ represents hydrogen atom or methyl group, a is 1 or 2.

In the betaine ester (II), each of $R^1$ and $R^2$ is preferably a group having from 1 to 4 carbon atoms, more preferably methyl group. $R^3$ is preferably a group having from 1 to 22 carbon atoms. Preferably, n is from 0 to 3. Examples of the anion represented by $X^-$ include halogen ions, sulfate ion, hydrogensulfate ion and perchlorate ion, of which chlorine ion is preferred.

Also, the following can be cited as illustrative examples of the group represented by $R^4$.

(1) Saturated or unsaturated, substituted or unsubstituted aliphatic hydrocarbon group having from 1 to 11 carbon atoms:

A reside in which one hydroxyl group is removed from an aliphatic alcohol such as ethanol, leaf alcohol (cis-3-hexenol), 3-octenol, 2,4-dimethyl-3-cyclohexene-1-methanol, 4-isopropylcyclohexanol, 4-isopropylcyclohexylmethanol, 1-(4-isopropylcyclohexyl) ethanol, p-t-butylcyclohexanol, o-t-butylcyclohexanol, 9-decenol, linalool, geraniol, nerol, citronellol, rhodinol, dimethyloctanol, hydroxycitronellol, tetrahydrolinalool, lavandulol, mugol, myrcenol, terpineol, L-menthol, borneol, isopulegol, tetrahydromugol, nopol or glycerol.

(2) Substituted or unsubstituted aromatic hydrocarbon group having from 1 to 11 carbon atoms:

A reside in which one hydroxyl group is removed from an aromatic alcohol such as benzyl alcohol, β-phenylethyl alcohol, γ-phenylpropyl alcohol, cinnamic alcohol, anisic alcohol, dimethylbenzylcarbinol, methylphenylcarbinol, dimethylphenylcarbinol, phenoxyethyl alcohol, styrallyl alcohol, dimethylphenylethylcarbinol, thymol, carvacrol, eugenol, isoeugenol, ethyl vanillin, metha-chloroxylenol, 2,4-dichlorophenol, 2,4-dichlorobenzyl alcohol, hinokithiol or 3-methyl-4-isopropylphenol.

(3) Alkadienyl group or alkatrienyl group having from 12 to 30 carbon atoms:

A reside in which one hydroxyl group is removed from a compound such as farnesol or nerolidol.

(4) Aryl group or arylalkyl group having from 12 to 30 carbon atoms:

A reside in which one hydroxyl group is removed from a compound such as 2,2-dimethyl-3-(3-methylphenyl) propanol, 3-methyl-5-phenylpentanol, phenylethylmethylethylcarbinol, trichlosan, capsaicin or tocopherol.

(5) Monocyclic, bicyclic or tricyclic terpene hydrocarbon group having from 12 to 30 carbon atoms:

A reside in which one hydroxyl group is removed from a compound such as ambrinol, 1-(2-t-butylcyclohexyloxy)-2-butanol, pentamethylcyclohexylpropanol, 1-(2,2,6-trimethylcyclohexyl)-3-hexanol, santalol, cedrol, vetiverol or patchouli alcohol.

Since the functional alcohol releasing substance of the invention can release functional alcohols such as perfumes and antibacterial and antifungal agents gradually for a prolonged period of time, it can be used alone or in combination with other components as ingredients of, e.g., soaps, shampoos, detergents, cosmetics, spray products, deodorants, aromatics, bathing goods, coloring agents, hair colors, antibacterial agents, antifungal agents, vapor proofing agents, bedclothes, towels, clothes, tissues, sands for pet toilet use, chewing gums, cosmetics for pack use, clay compositions for handicraft use, absorbable articles, cosmetics for massage use, paints, agricultural chemicals, medicaments and inks.

The composition of the invention contains the functional alcohol releasing substance, and the amount of the functional alcohol releasing substance to be contained in the composition of the invention is preferably from 0.01 to 90% by weight, more preferably from 0.5 to 50% by weight, based on the composition, though it varies depending, e.g., on the kind of composition and the kind of functional alcohol of interest.

The composition of the invention is particularly useful as, e.g., a softening agent composition containing a textile conditioner or softening agent component, a detergent composition for clothing use containing a detergent component or a detergent composition for hard surface use.

Examples of the textile conditioner or softening agent component include quaternary ammonium salts, amines and neutral salts of amines, particularly an acid salt of a quaternary ammonium compound or tertiary amine compound having in its molecule one or more ester groups and/or amido groups and two or more alkyl groups or alkenyl groups having from 11 to 20 carbon atoms, an acid salt of a quaternary ammonium compound or tertiary amine compound having in its molecule one alkyl group or alkenyl group having from 11 to 20 carbon atoms and an amphoteric surface active agent having in its molecule one alkyl group or alkenyl group having from 6 to 20 carbon atoms. Also, for the purpose of further improving the softening performance, an alkylene oxide addition product of a higher alcohol or amine, a higher fatty acid or a salt thereof may be added as occasion demands. The amount of the textile conditioner or softening agent component to be used in the composition of the invention is preferably from 1 to 50% by weight, more preferably from 5 to 20% by weight.

Examples of the detergent component to be used in the composition of the invention include anionic surface active agents such as a polyoxyalkylene alkyl ether sulfate, an alkyl sulfate, an alkylbenzene sulfonate, an α-olefin sulfonate, an alkane sulfonate, a fatty acid salt, an α-sulfofatty acid ester salt, a polyoxyalkylene alkyl ether carboxylate and a polyoxyalkylene alkyl ether phosphate, nonionic surface active agents such as a polyoxyalkylene alkyl ether, an alkyl glucoside, mono- and dialkanolamides of a fatty acid and an active agent of Pluronic system, cationic surface active agents such as a quaternary ammonium salt and amphoteric surface active agents such as carbobetaine and sulfobetaine. Amount of the detergent component in the composition of the invention is preferably from 1 to 80% by weight, more preferably from 20 to 40% by weight, as a detergent composition for clothing use. As a detergent composition for hard surface use, it is preferably from 0.5 to 60% by weight, more preferably from 1 to 50% by weight, based on the composition.

As occasion demands, other additive agents used in general softening agents and detergents can be optionally added to the composition of the invention within such a range that they do not spoil effects of the invention.

Examples of the other additive agents which can be added include storage stabilizing agents such as lower alcohols including ethanol and isopropanol, a glycol, a polyol and alkylene oxide addition products thereof; chelating agents such as ethylenediamine tetraacetate, diethylenetriamine pentaacetate, sodium acid pyrophosphate, tetrasodium pyrophosphate, sodium tripolyphosphate, zeolite, ethylhydroxy diphosphonate, citric acid, dipicolinic acid, picolinic acid and 8-hydroxyquinoline; solubilizing agents such as sodium salts and potassium salts of toluenesulfonic acid and xylenesulfonic acid and urea; alkali agents such as sodium carbonate and an amorphous alkali metal silicate; viscosity adjusting agents such as a clay mineral and a water-soluble polymer; moisture keeping agents such as glycerol and sorbitol; feel improving agents such as cationic cellulose; extenders such as sodium sulfate; and a pH adjusting agent, a hydrotropic agent, an antifoaming agent, an antioxidant, an enzyme, a perfume, an antibacterial agent, a pigment and an antiseptic/antifungal agent.

EXAMPLES

Unless otherwise noted, the term "part" and "%" in the examples are weight basis.

Synthesis Example 1

Synthesis of N-octadecanoyl-N',N'-dimethyl-1,3-diaminopropane

A 300 g (1.05 mol) portion of octadecanoic acid was put into a flask and melted by stirring at 180° C. in an atmosphere of nitrogen. To this was added dropwise 113.1 g (1.11 mol) of N,N-dimethyl-1,3-diaminopropane spending 3 hours, thereby effecting the reaction while evaporating the generated water. After completion of the dropwise addition, this was further stirred at 180° C. for 4 hours in an atmosphere of nitrogen. Thereafter, the unreacted material amine remained in the reaction mixture was evaporated under a reduced pressure to obtain the title compound as a light brown waxy solid (melting point 64–67° C.).

Synthesis Examples 2 to 4

Hexadecanoic acid, dodecanoic acid or octanoic acid was used instead of octadecanoic acid, and these fatty acids were allowed to react with N,N-dimethyl-1,3-diaminopropane in the same manner as described in Synthesis Example 1 to obtain N-hexadecanoyl-N',N'-dimethyl-1,3-diaminopropane, N-decanoyl-N',N'-dimethyl-1,3-diaminopropane and N-octanoyl-N',N'-dimethyl-1,3-diaminopropane, respectively.

Synthesis Example 5

Synthesis of N-acetyl-N',N'-dimethyl-1,3-diaminopropane

A 51.1 g (0.50 mol) portion of N,N-dimethyl-1,3-diaminopropane was put into a flask and cooled to 5° C. while stirring in an atmosphere of nitrogen. Under ice-cooling, to this was added dropwise 51.1 g (0.50 mol) of acetic anhydride spending 1 hour. After completion of the dropwise addition, this was further stirred at 25° C. for 3 hours. Thereafter, the reaction mixture was again ice-cooled and 41.6 g (0.5 mol) of 48% sodium hydroxide aqueous solution was added dropwise thereto spending 15 minutes and then, after completion of the dropwise addition, 350 ml of acetone was added to the reaction mixture and allowed to stand at room temperature for 8 hours. Sodium acetate precipitated in the acetone solution was removed by filtration, acetone was evaporated under a reduced pressure and then 71 g of the remaining yellow oil was distilled under a reduced pressure to obtain the title compound as a transparent oil. Yield 62.4 g (0.433 mol; yield 86.8%, boiling point 116–118° C./0.64 kPa).

Synthesis Example 6

Synthesis of 3-methyl-5-phenylpentyl chloroacetate

A 127.05 g (1.125 mol) of chloroacetyl chloride and 200 ml of dichloromethane were put into a flask and, while stirring under ice-cooling, a mixture consisting of 199.6 g (1.12 mol) of 3-methyl-5-phenylpentanol and 88.59 g (1.12 mol) of pyridine was added dropwise thereto spending 2 hours (reaction temperature 5 to 15° C.). After completion of the dropwise addition, this was further stirred at room temperature for 3 hours, and white crystals of the thus precipitated pyridine hydrochloride were removed by filtration. The reaction mixture was washed with water (3×300 ml), the organic phase was dehydrated with anhydrous magnesium sulfate and then the solvent was evaporated under a reduced pressure. By distilling the remained yellow oil under a reduced pressure, the title compound was obtained as a light yellow transparent oil. Yield 242.25 g (0.849 mol; yield 84.9%, boiling point 148–151° C./0.2 kPa).

Synthesis Example 7

Synthesis of L-menthyl chloroacetate

By the same method of Synthesis Example 6, the title compound was obtained as a light yellow transparent oil from chloroacetyl chloride and L-menthol. Boiling point 102–106° C./0.027 kPa.

Synthesis Example 8

Synthesis of geranyl chloroacetate

By the same method of Synthesis Example 6, the title compound was obtained as a light yellow transparent oil from chloroacetyl chloride and geraniol. Boiling point 113–115° C./0.13 kPa.

Synthesis Example 9

Synthesis of cis-3-hexenyl chloroacetate

By the same method of Synthesis Example 6, the title compound was obtained as a transparent oil from chloroacetyl chloride and cis-3-hexenol. Boiling point 89–92° C./0.13 kPa.

Synthesis Example 10

Synthesis of 2-phenylethyl chloroacetate

By the same method of Synthesis Example 6, the title compound was obtained as a transparent oil from chloroacetyl chloride and 2-phenylethyl alcohol. Boiling point 121–123° C./0.69 kPa.

Synthesis Example 11

Synthesis of 3-methyl-4-isopropylphenyl chloroacetate

By the same method of Synthesis Example 6, chloroacetyl chloride was allowed to react with 3-methyl-4-isopropylphenol, the reaction mixture was washed with water and then the solvent was evaporated under a reduced pressure to obtain the title compound as a transparent oil. The title compound was used in the subsequent reaction without distillation.

Synthesis of 3-methyl-4-isopropylphenyl chloroacetate

A 36.86 g (0.100 mol) portion of N-octadecanoyl-N',N'-dimethyl-1,3-diaminopropane and 100 ml of chloroform were put into a flask, and 23.30 g (0.101 mol) of geranyl chloroacetate was added thereto at 25° C. spending 5 minutes. The reaction mixture was stirred at 25° C. for 36 hours and then, after confirming by $^1$H-NMR that chloroacetate was mostly disappeared, the solvent was evaporated under a reduced pressure. The thus obtained viscous oil was dissolved in 200 ml of acetone and cooled to 5 to 10° C. to effect precipitation of a white precipitate. The supernatant solvent was discarded, and the precipitated was collected and dried under a reduced pressure to obtain the title compound (to be referred to as betaine ester (1) hereinafter) as a slightly brownish white solid. Yield 49.1 g (0.0819 mol; yield 81.9%).

$^1$H-NMR (200 MHz, CDCl$_3$): δ[ppm]0.88 (3H, t, J=6.4 Hz, —(CH$_2$)$_{16}$—CH$_3$), 1.26 (28H, br s, —(CH$_2$)$_{14}$—CH$_3$), 1.5–1.7 (2H, m, —CH$_2$—CH$_2$—CONH—), 1.61 (3H, s, C H$_3$—C=CH—CH$_2$—O), 1.69 (3H, s, (CH$_3$)CH$_3$C=C), 1.73 (3H, s, (CH$_3$)CH$_3$C=C), 1 8–2.3 (6H, br s, N—C—CH$_2$—C—N, CH$_3$—C—CH$_2$—CH$_2$—C=C (CH$_3$)$_2$) 2.29 (2 H, t, J=7.6 Hz, —CH$_2$—CH$_2$—CONH—), 3.37 (2H, dt, J=5, J=7.6 Hz, —CONH—CH$_2$—C—), 3.49 (6H, s, CH$_3$—N$^+$—CH$_3$), 4.1 (2H, t, J=7.8 Hz, —CH$_2$—CH$_2$—N$^+$—), 4.66 (2H, s, N$^+$—CH$_2$—C=O), 4.72 (2H, d, J=7.3 Hz, O—CH$_2$—CH=C—), 5.05 (1H, m, —CH—C=C(CH$_3$)$_2$), 5.31 (1H, t, J=7.3 Hz, O—CH$_2$—CH=C—), 8.01 (1H, t, J=5 Hz, —CONH—)

IR (NaCl) [cm$^{-1}$] 3700–3100, 3292 (ν NH, amide), 3020 (ν CH, =CH—), 2954 (ν $_{as}$CH$_3$), 2924 (ν $_{as}$CH$_2$), 2852 (ν $_s$CH$_2$), 1747 (ν C=O, ester), 1645 (ν C=O, amide), 1552 (δ NH, ν C—N), 1464 (δ $_{as}$δCH$_3$; δ CH$_2$), 1377 (δ $_s$CH$_3$) 1198 (ν C—O, ester), 1124, 1020, 984, 719 ((CH$_2$)$_n$).

Inventive Example 2

Synthesis of N,N-dimethyl-N-geranyloxycarbonylmethyl-N-(3-(hexadecanoylamino)propyl)ammonium chloride The reaction of Inventive Example 1 was repeated, except that 34.59 g (0.10 mol) of N-hexadecanoyl-N',N'-dimethyl-1,3-diaminopropane was used instead of N-octadecanoyl-N',N'-dimethyl-1,3-diaminopropane, and the solvent was evaporated under a reduced pressure. The thus obtained viscous oil was dissolved in 200 ml of acetonitrile instead of acetone and then the title compound (to be referred to as betaine ester (2) hereinafter) was obtained as a yellow viscous solid in the same manner as described in Inventive Example 1. Yield 50.11 g (0.0877 mol; yield 87.7%).

$^1$H-NMR (200 MHz, CDCl$_3$): δ[ppm] 0.88 (3H, t, J=6.4 Hz, —(CH$_2$)$_{14}$—CH$_3$), 1.26 (24H, br s, —(CH$_2$)$_{12}$—CH$_3$), 1.5–1.7 (2H, m, —CH$_2$—CH$_2$—CONH—), 1.61 (3H, s, C H$_3$—C=CH—CH$_2$—O), 1.69 (3H, s, (CH$_3$)CH$_3$C=C), 1.73 (3H, s, (CH$_3$)CH$_3$C=C), 1 8–2.3 (6H, br s, N—C—CH$_2$—C—N, CH$_3$—C—CH$_2$—CH$_2$—C=C(CH$_3$)$_2$), 2.29 (2H, t, J=7.6 Hz, —CH$_2$—CH$_2$—CONH—), 3.37 (2H, dt, J=5, J=7.6 Hz, —CONH—CH$_2$—C—), 3.49 (6H, s, CH$_3$—N$^+$—CH$_3$), 4.1 (2H, t, J=7.8 Hz, —CH$_2$—CH$_2$—N$^+$—), 4.66 (2H, s, N$^+$—CH$_2$—C=O), 4.72 (2H, d, J=7.3 Hz, O—CH$_2$—CH=C—), 5.05 (1H, m, —CH—C=C(CH$_3$)$_2$), 5.31 (1H, t, J=7.3 Hz, O—CH$_2$—CH=—), 8.01 (1H, t, J=5 Hz, —CONH—)

IR (NaCl) [cm$^{-1}$] 3700–3100, 3320 (ν NH, amide), 3020 (ν CH, =CH—), 2954 (ν $_{as}$CH$_3$), 2924 (ν $_{as}$CH$_2$), 2852 (ν $_s$ CH$_2$), 1747 (ν C=O, ester), 1649 (ν C=O, amide), 1547 (δ NH, ν C—N), 1466 (δ $_{as}$CH$_3$; δ CH$_2$), 1379 (δ $_s$CH$_3$), 1198 (ν C—O, ester), 721 ((CH$_2$)$_n$).

Inventive Example 3

Synthesis of N,N-dimethyl-N-geranyloxycarbonylmethyl-N-(3-(dodecanoylamino) propyl)ammonium chloride A 22.76 g (0.080 mol) portion of N-dodecanoyl-N',N'-dimethyl-1,3-diaminopropane and 120 ml of diethyl ether were put into a flask, and 18.46 g (0.080 mol) of geranyl chloroacetate was added thereto at 25° C. spending 5 minutes. The reaction mixture was stirred at 25° C. for 24 hours, and disappearance of the most part of chloroacetate was confirmed by $^1$H-NMR. Next, the reaction mixture was slowly added dropwise to 600 ml of hexane which was ice-cooled and vigorously stirred, spending 10 minutes, to effect precipitation of the product as a white solid. Thereafter, in the same manner as described in Inventive Example 1, the title compound (to be referred to as betaine ester (3) hereinafter) was obtained as a light yellow viscous oil. Yield 38.50 g (0.0747 mol; yield 93.4%).

$^1$H-NMR (200 MHz, CDCl$_3$): δ[ppm] 0.88 (3H, t, J=6.4 Hz, —(CH$_2$)$_{10}$—CH$_3$), 1.26 (16H, br s, —(CH$_2$)$_2$—CH$_3$), 1.5–1.7 (2H, m, —CH$_2$—CH$_2$—CONH—), 1.61 (3H, s, C C$\underline{H}_3$—C=CH—CH$_2$—O), 1.69 (3H, s, (C$\underline{H}_3$)CH$_3$C=C), 1.73 (3H, s, (C$\underline{H}_3$)CH$_3$C=C), 1 8–2.3 (6H, br s, N—C—CH$_2$—C—N, CH$_3$—C—C$\underline{H}_2$—C$\underline{H}_2$—C=C(CH$_3$)$_2$), 2.29 (2H, t, J=7.6 Hz, —CH$_2$—C$\underline{H}_2$—CONH—), 3.37 (2H, dt, J=5, J=7.6 Hz, —CONH—C$\underline{H}_2$—C—), 3.49 (6H, s, CH$_3$—N$^+$—CH$_3$), 4.1 (2H, t, J=7.8 Hz, —CH$_2$—C$\underline{H}_2$—N$^+$—), 4.66 (2H, s, N$^+$—CH$_2$—C=O), 4.72 (2H, d, J=7.3 Hz, O—C$\underline{H}_2$—CH=C—), 5.05 (1H, m, —C$\underline{H}$—C=C(CH$_3$)$_2$), 5.31 (1H, t, J=7.3 Hz, O—CH$_2$—C$\underline{H}$=—), 8.01 (1H, t, J=5 Hz, —CONH—)

IR (NaCl) [cm$^{-1}$] 3700–3100, 3244 (ν NH, amide), 3051, 3022 (ν CH, =CH—), 2954 (ν $_{as}$CH$_3$), 2924 (ν $_{as}$CH$_2$), 2854 (ν $_s$ CH$_2$), 1747 (ν C=O, ester), 1651 (ν C=O, amide), 1549 (δ NH, ν C—N), 1485, 1466 (δ $_{as}$CH$_3$; δ CH$_2$), 1377 (δ $_s$CH$_3$), 1225, 1198 (ν C—O, ester), 1155, 1124, 1020, 987, 935, 899, 721 ((CH$_2$)$_n$).

Inventive Example 4

Synthesis of N,N-dimethyl-N-geranyloxycarbonylmethyl-N-(3-(octanoylamino)propyl)ammonium chloride A 22.84 g (0.100 mol) portion of N-octanoyl-N',N'-dimethyl-1,3-diaminopropane and 250 ml of diethyl ether were put into a flask, and 24.23 g (0.105 mol) of geranyl chloroacetate was added thereto at 0 to 5° C. spending 10 minutes. The reaction mixture was stirred at 5 to 25° C. for 24 hours, and disappearance of the most part of chloroacetate was confirmed by $^1$H-NMR. Next, the reaction mixture was slowly added dropwise to 650 ml of pentane which was ice-cooled and vigorously stirred, spending 10 minutes, to effect precipitation of the product as a white solid. Thereafter, in the same manner as described in Inventive Example 1, the title compound (to be referred to as betaine ester (4) hereinafter) was obtained as a light yellow viscous oil. Yield 38.2 g (0.0832 mol; yield 83.2%).

$^1$H-NMR (200 MHz, CDCl$_3$): δ[ppm] 0.88 (3H, t, J=6.4 Hz, —(CH$_2$)$_6$—C$\underline{H}_3$), 1.26 (8H, br s, —(C$\underline{H}_2$)$_4$—CH$_3$), 1.5–1.7 (2H, m, —C$\underline{H}_2$—CH$_2$—CONH—), 1.61 (3H, s, C$\underline{H}_3$)—C=CH—CH$_2$—O), 1.69 (3H, s, (C$\underline{H}_3$)CH$_3$C=C), 1.73 (3H, s, (C$\underline{H}_3$)CH$_3$C=C), 1 8–2.3 (6H, br s, N—C—CH$_2$—C—N, CH$_3$—C—C$\underline{H}_2$—C$\underline{H}_2$—C=C(CH$_3$)$_2$), 2.29 (2H, t, J=7.6 Hz, —CH$_2$—C$\underline{H}_2$—CONH—), 3.37 (2H, dt, J 5, J=7.6 Hz, —CONH—C$\underline{H}_2$—C—), 3.49 (6H, s, CH$_3$—N$^+$—CH$_3$), 4.1 (2H, t, J=7.8 Hz, —CH$_2$—C$\underline{H}_2$—N$^+$—), 4.66 (2H, s, N$^{+-CH}{}_2$—C=O), 4.72 (2H, d, J=7.3 Hz, O—C$\underline{H}_2$—CH=C—), 5.05 (1H, m, —C$\underline{H}$—C=C(CH$_3$)$_2$), 5.31 (1H, t, J=7.3 Hz, O—CH$_2$—C$\underline{H}$=C—), 8.01 (1H, t, J=5 Hz, —CONH—)

IR (NaCl) [cm$^{-1}$] 3700–3100, 3244 (ν NH, amide), 3051, 3022 (ν CH, =CH—), 2954 (ν $_{as}$CH$_3$), 2924 (ν $_{as}$CH$_2$), 2854 (ν $_s$CH$_2$), 1745 (ν C=O, ester), 1655 (ν C=O, amide), 1549 (δ NH, ν C—N), 1485, 1466 (δ $_{as}$CH$_3$; δ CH$_2$), 1377 (δ $_s$CH$_3$), 1225, 1198 (ν C—O, ester), 1155, 1124, 1020, 987, 935, 899, 721 ((CH$_2$)$_n$).

Inventive Example 5

Synthesis of N,N-dimethyl-N-geranyloxycarbonylmethyl-N-(3-(acetylamino)propyl)ammonium chloride A 7.21 g (0.05 mol) portion of N-acetyl-N',N'-dimethyl-1,3-diaminopropane and 150 ml of diethyl ether were put into a flask, and 11.65 g (0.0505 mol) of geranyl chloroacetate was added thereto at 0 to 5° C. spending 10 minutes. The reaction mixture was stirred for 2 hours while cooling on ice to observe precipitation of the product. This was further stirred at 25° C. for 12 hours, and disappearance of the most part of chloroacetate was confirmed by $^1$H-NMR. Next, the solvent was evaporated under a reduced pressure, and the reaction mixture as the residual viscous oil was dissolved in 20 ml of dichloromethane and slowly added dropwise to 400 ml of diethyl ether which was ice-cooled and vigorously stirred, spending 5 minutes, to effect precipitation of the product as a white solid. Thereafter, in the same manner as described in Inventive Example 1, the title compound (to be referred to as betaine ester (5) hereinafter) was obtained as a light yellow viscous oil. Yield 15.6 g (41.6 mmol; yield 83.2%).

$^1$H-NMR (200 MHz, CDCl$_3$): δ[ppm] 1.61 (3H, s, C$\underline{H}_3$—C=CH—CH$_2$—O), 1.69 (3H, s, (C$\underline{H}_3$)CH$_3$C=C), 1.73 (3H, s, (C$\underline{H}_3$)CH$_3$C=C), 2.05 (3H, s, CH$_3$—CONH—), 1 9–2.2 (6H, N—C—CH$_2$—C—N, (CH$_3$)C—C$\underline{H}_2$—C$\underline{H}_2$—C=C), 3.36 (2H, dt, J=5.5, J=7.6 Hz, —CONH—C$\underline{H}_2$—C—), 3.51 (6H, s, CH$_3$—N$^+$—CH$_3$), 4.08 (2H, t, J=7.6 Hz, —CH$_2$—C$\underline{H}_2$—N$^+$—), 4.64 (2H, s, N$^+$—CH$_2$—C=O), 4.73 (2H, d, J=7.3 Hz, O—C$\underline{H}_2$—CH=C—), 5.05 (1H, m, —C$\underline{H}$—C=C(CH$_3$)$_2$), 5.31 (1H, t, J=7.3 Hz, O—CH$_2$—C$\underline{H}$=C—), 8.25 (1H, t, J=5.5 Hz, —CONH—)

IR (NaCl) [cm$^{-1}$] 3700–3100, 3242, 3057, 3020 (ν CH,=CH—), 2968 (ν $_{as}$CH$_3$), 2929 (ν $_{as}$CH$_2$), 2858 (ν $_s$CH$_2$), 1743 (ν C=O, ester), 1660 (ν C=O, amide), 1552 (δ NH, ν C—N), 1485, 1444, 1408, 1375 (δ $_s$CH$_3$; CH$_3$—CONH—), 1279, 1198 (ν C—O, ester), 1161, 1111, 1018, 933, 894, 727 (—CH$_2$—).

Inventive Example 6

Synthesis of N,N-dimethyl-N-(3-methyl-5-phenylpentyl)oxycarbonylmethyl-N-(3-(octadecanoylamino)propyl)ammonium chloride The title compound (to be referred to as betaine ester (6) hereinafter) was obtained as a white solid in the same manner as described in Inventive Example 1, except that 25.73 g (0.101 mol) of 3-methyl-5-phenylpentyl chloroacetate was used instead of geranyl chloroacetate. Yield 50.8 g (0.0815 mol; yield 81.5%).

$^1$H-NMR (200 MHz, CDCl$_3$): δ[ppm] 0.88 (3H, t, J=6.4 Hz, —(CH$_2$)$_6$—C$\underline{H}_3$), 0.98 (3H, d, J=6 Hz, —CH—C$\underline{H}_3$), 1.25 (28H, br s, —(C$\underline{H}_2$)$_{14}$—CH$_3$), 1.4–1.85 (7H, —C$\underline{H}_2$—CH(CH$_3$)C$\underline{H}_2$—, —C$\underline{H}_2$—CH$_2$—CONH—), 2.06 (2H, m, N—C—CH$_2$—C—N), 2.28 (2H, t, J=7.6 Hz, —CH$_2$—C$\underline{H}_2$—CONH—), 2.65 (2H, dddd, J=7.6, 7.6, 5.5, 5.5 Hz, Ph—C$\underline{H}_2$—CH$_2$—), 3.36 (2H, dt, J=5.5, J=7.6 Hz, —CONH—C$\underline{H}_2$—C—), 3.47 (6H, s, CH$_3$—N$^+$—CH$_3$), 4.05 (2H, t, J=7.6 Hz, —CH$_2$—C$\underline{H}_2$—N$^+$—), 4.24 (2H, t, J=6.5 Hz, —C$\underline{H}_2$—O—C=O), 4.59 (2H, s, N$^{30}$—C$\underline{H}_2$—C=O), 7.0–7.35 (5H, m, phenyl), 7.95 (1H, t, J=5.5 Hz, —CONH—)

IR (NaCl) [cm$^{-1}$] 3700–3100, 3292 (ν NH), 3026 (ν CH, phenyl), 2954 (ν $_{as}$CH$_3$), 2922 (ν $_{as}$CH$_2$), 2850 (ν CH$_2$), 1745 (ν C=O, ester), 1639 (ν C=O, amide), 1552 (δ NH, ν C—N), 1467 (δ $_{as}$CH$_3$; δ CH$_2$, phenyl), 1379 (δ $_s$CH$_3$), 1203 (ν C—O, ester), 1026 (δ CH, phenyl), 744 (phenyl), 721 ((CH$_2$)$_n$), 698 (phenyl).

Inventive Example 7

Synthesis of N,N-dimethyl-N-(3-methyl-5-phenylpentyl)oxycarbonylmethyl-N-(3-(dodecanoylamino)propyl)ammonium chloride The title compound (to be referred to as betaine ester (7) hereinafter) was obtained as a yellow viscous oil in the same manner as described in Inventive Example 3, except that 28.45 g (0.1 mol) of N-dodecanoyl-N',N'-dimethyl-1,3-diaminopropane was used, and 25.73 g (0.101 mol) of 3-methyl-5-phenylpentyl chloroacetate was used instead of geranyl chloroacetate. Yield 45.83 g (0.085 mol; yield 85%).

$^1$H-NMR (200 MHz, CDCl$_3$): δ[ppm] 0.88 (3H, t, J=6.4 Hz, —(CH$_2$)$_{16}$—CH$_3$), 0.98 (3H, d, J=6 Hz, —CH—CH$_3$ ), 1.25 (16H, br s, —(CH$_2$)$_8$—CH$_3$), 1.4–1.85 (7H, —CH$_2$—C H(CH$_3$)—CH$_2$—, —CH$_2$—CH$_2$—CONH—), 2.06 (2H, m, N—C—CH$_2$—C—N), 2.28 (2H, t, J=7.6 Hz, —CH$_2$—C H$_2$—CONH—), 2.65 (2H, dddd, J=7.6, 7.6, 5.5, 5.5 Hz, Ph—CH$_2$—CH$_2$—), 3.36 (2H, dt, J=5.5, J=7.6 Hz, —CONH—CH$_2$—C—), 3.47 (6H, s, CH$_3$—N$^+$—CH$_3$), 4.05 (2H, t, J=7.6 Hz, —CH$_2$—CH$_2$—N$^+$—), 4.24 (2H, t, J=6.5 Hz, —CH$_2$—O—C=O), 4.59 (2H, s, N$^+$—CH$_2$—C=O), 7.0–7.35 (5H, m, phenyl), 7.95 (1H, t, J=5.5 Hz, —CONH—)

IR (NaCl) [cm$^{-1}$] 3700–3100, 3026 (ν CH, phenyl), 2954 (ν $_{as}$CH$_3$), 2924 (ν $_{as}$CH$_2$), 2854 (ν $_s$CH$_2$), 1743 (ν C=O, ester), 1651 (ν C=O, amide), 1547 (δ NH, ν C—N), 1493 (phenyl), 1466 (δ $_{as}$CH$_3$; δ CH$_2$), 1379 (δ $_s$CH$_3$), 1203 (ν C—O, ester), 1026 (δ CH, phenyl), 744 (phenyl), 721 ((CH$_2$)$_n$), 698 (phenyl).

Inventive Example 8

Synthesis of N,N-dimethyl-N-cis-3-hexenyloxycarbonylmethyl-N-(3-(acetylamino)propyl)ammonium chloride The title compound (to be referred to as betaine ester (8) hereinafter) was obtained as a transparent glassy substance in the same manner as described in Inventive Example 5, except that 8.65 g (0.060 mol) of N-acetyl-N',N'-dimethyl-1,3-diaminopropane was used, and 11.13 g (0.063 mol) of cis-3-hexenyl chloroacetate was used instead of geranyl chloroacetate. Yield 15.4 g (0.048 mol; yield 80%).

$^1$H-NMR (200 MHz, CDCl$_3$): δ[ppm]

0.98 (3H, t, J=7.5 Hz, —CH$_2$—CH$_3$), 1.8–2.2 (4H, CH$_3$—CH$_2$—C=C—, N—CH$_2$—C—N), 2.04 (3H, s, C H$_3$—CONH—), 2.42 (2H, q, J=7 Hz, —O—CH$_2$—C H$_2$—CH=C), 3.36 (2H, dd, J=5.5, 7.2 Hz, —CONH—C H$_2$—C—), 3.52 (6H, s, CH$_3$—N$^+$—CH$_3$), 4.05 (2H, t, J=7.2 Hz, —CH$_2$—CH$_2$—N$^+$—), 4.20 (2H, t, J=7 Hz, —O—C H$_2$—CH$_2$), 4.66 (2H, s, N$^+$—CH$_2$—C=O), 5.36 (1H, dt, J=10.8, 7.2 Hz, —C=CH—), 5.55 (1H, dt, J=10.8, 7.2 Hz, —CH=C—), 8.25 (1H, t, J=5.5 Hz, —CONH—)

IR (NaCl) [cm$^{-1}$] 3700–3100, 3080 (ν CH, =CH—), 3012 (ν CH, =CH—), 2966 (ν $_{as}$CH$_3$), 2875 (ν $_s$CH$_2$), 1747 (ν C=O, ester), 1655 (ν C=O, amide), 1556 (δ NH, ν C—N), 1483, 1462 (δ $_{as}$CH$_3$; δ CH$_2$), 1408 (δ CH$_2$), 1371 (δ $_s$CH$_3$), 1300, 1201 (ν C—O, ester), 1020, 899.

Inventive Example 9

Synthesis of N,N-dimethyl-N-L-menthyloxycarbonylmethyl-N-(3-(acetylamino)propyl)ammonium chloride A 7.21 g (0.05 mol) portion of N-acetyl-N',N'-dimethyl-1,3-diaminopropane and 25 ml of diethyl ether were put into a flask, and 11.64 g (0.05 mol) of L-menthyl chloroacetate was added thereto at 0 to 5° C. spending 5 minutes. The reaction mixture was stirred at 25° C. for 48 hours, and disappearance of the most part of chloroacetate was confirmed by $^1$H-NMR. After evaporation of the solvent under a reduced pressure, the crude product was dissolved in 30 ml of dichloromethane and then the reaction mixture was slowly added dropwise to 480 ml of hexane which was ice-cooled and vigorously stirred, spending 10 minutes, to effect precipitation of the product as an oily substance. When the supernatant solvent was discarded and 150 ml of diethyl ether was added to the oily substance, the oily substance was solidified. The supernatant organic solvent was discarded and then the white solid was collected and dried under a reduced pressure to obtain the title compound (to be referred to as betaine ester (9) hereinafter) as a white powder. Yield 14.75 g (0.039 mol; yield 78.2%).

$^1$H-NMR (200 MHz, CDCl$_3$): δ[ppm] 0.88 (3H, d, J=6.9 Hz, >CH$_2$—CH$_3$), 0.90 (3H, d, J=5.5 Hz, (CH$_3$)$_2$—CH—), 0.93 (3H, d, J=5.5 Hz, (CH$_3$)$_2$—CH—), 1.05 (2H, quint, J=11 Hz, >CH$_2$), 1.43 (2H, t, J=11 Hz, >CH$_2$), 1.69 (2H, d, J=11 Hz, >CH$_2$), 1 87 (1H, ddddd, J=7, 7, 7, 7, 3 Hz, >CH), 1.9–2.2 (3H, >CH, N—C—CH$_2$—C—N), 2.06 (3H, s, C H$_3$—CONH—), 3.36 (2H, dt, J=5.5, 7.2 Hz, —CONH—C H$_2$—C—), 3.51 (3H, s, CH$_3$—N$^+$—CH$_3$), 3.53 (3H, s, CH$_3$—N$^+$—CH$_3$), 4.13 (2H, t, J=7 Hz, —CH$_2$—C H$_2$—N$^+$—), 4.43 (1H, d, N$^+$—CH$_2$—C=O, J=16 Hz), 4.62 (1H, d, N$^+$—CH$_2$—C=O, J=16 Hz), 4.79 (1H, td, J=4.4, 10.9 Hz, >CH—O—C=O), 8.35 (1H, t, J=5.5 Hz, —CONH—).

Inventive Example 10

Synthesis of N,N-dimethyl-N-L-menthyloxycarbonylmethyl-N-(3-(dodecanoylamino)propyl)ammonium chloride A 28.45 g (0.100 mol) portion of N-dodecanoyl-N',N'-dimethyl-1,3-diaminopropane and 120 ml of diethyl ether were put into a flask, and 23.27 g (0.100 mol) of L-menthyl chloroacetate was added thereto at 0 to 5° C. spending 5 minutes. The reaction mixture was stirred at 25° C. for 48 hours, and disappearance of the most part of chloroacetate was confirmed by $^1$H-NMR. After evaporation of the solvent under a reduced pressure, the crude product was dissolved in 30 ml of dichloromethane, and the reaction mixture was slowly added dropwise to 480 ml of pentane which was ice-cooled and vigorously stirred, spending 10 minutes, to effect precipitation of the product as an oily substance. The oily substance was collected by discarding the supernatant solvent and again added dropwise to 480 ml of pentane and the same step was repeated, and then the supernatant pentane was discarded and the precipitate was collected and dried under a reduced pressure to obtain the title compound (to be referred to as betaine ester (10) hereinafter) as a light yellow transparent oil. Yield 38.65 g (0.075 mol; yield 74.7%).

$^1$H-NMR (200 MHz, CDCl$_3$): δ[ppm] 0.76 (3H, d, J=6.9 Hz, >CH—CH$_3$), 0.90 (3H, d, J=5.5 Hz, (CH$_3$)$_2$—CH—), 0.93 (3H, d, J=5.5 Hz, (CH$_3$)$_2$—CH—), 1.05 (2H, quint, J=11 Hz, >CH$_2$), 1.25 (16H, br s, —(CH$_2$)$_2$—CH$_3$), 1.4–1.9 (7H, cyclic, >CH$_2$, —CH$_2$—CH$_2$—CONH—), 1.9–2.2 (3H, >CH, N—C—CH$_2$—C—N), 3.36 (2H, dt, J=5.5, 7.2 Hz, —CONH—CH$_2$—C—), 3.50 (3H, s, CH$_3$—N$^+$—CH$_3$), 3.52 (3H, s, CH$_3$—N$^+$—CH$_3$), 4.13 (2H, t, J=7 Hz, —CH$_2$—CH$_2$—N$^+$—), 4.43 (1H, d, N$^+$—CH$_2$—C=O, J=16 Hz), 4.62 (1H, d, N$^+$—CH$_2$—C=O, J=16 Hz), 4.82 (1H, td, J=4.5, 10.9 Hz, >CH—O—C=O), 8.35 (1H, t, J=5.5 Hz, —CONH—)

IR (NaCl) [cm$^{-1}$] 3700–3100, 2956 (ν $_{as}$CH$_3$), 2924 (ν $_{as}$ CH$_2$), 2854 (ν $_s$CH$_2$), 1741 (ν C=O, ester), 1651 (ν C=O, amide), 1549 (δ NH, ν C—N), 1466 (δ $_{as}$CH$_3$; δ CH$_2$), 1390 (gem-dimethyl), 1371 (gem-dimethyl), 1242, 1209 (ν C—O, ester), 1153, 1020, 951, 912, 721 ( (CH$_2$)$_n$).

Inventive Example 11

Synthesis of N,N-dimethyl-N-(2-phenylethyl)oxycarbonylmethyl-N-(3-(dodecanoylamino)propyl)ammonium chloride A 14.22 g (0.050 mol) portion of N-dodecanoyl-N',N'-dimethyl-1,3-diaminopropane and 120 ml of diethyl ether were put into a flask, and 9.93 g (0.050 mol) of 2-phenylethyl chloroacetate was added thereto at 0 to 5° C. spending 5 minutes. The reaction mixture was further stirred at 25° C. for 24 hours, and disappearance of the most part of chloroacetate was confirmed by $^1$H-NMR. Next, the reaction mixture was slowly added dropwise to 600 ml of hexane which was ice-cooled and vigorously stirred, spending 10 minutes, to effect precipitation of the product as a white solid. Thereafter, in the same manner as described in Inventive Example 1, the title compound (to be referred to as betaine ester (11) hereinafter) was obtained as a white powder. Yield 20.10 g (0.0416 mol; yield 83.2%).

$^1$H-NMR (200 MHz, CDCl$_3$): δ[ppm] 0.88 (3H, t, J=6.4 Hz, —(CH$_2$)$_{10}$—C<u>H</u>$_3$), 1.24 (16H, br s, —(C<u>H</u>$_2$)$_8$—CH$_3$), 1.5–1.8 (2H, m, —C<u>H</u>$_2$—CH$_2$—CONH—), 1.9–2.2 (2H, m, N—C—CH$_2$—C—N), 2.29 (2H, t, J=7.6 Hz, —CH$_2$—C<u>H</u>$_2$—CONH—), 2.98 (2H, t, J=7 Hz, —CH$_2$—C<u>H</u>$_2$—phenyl), 3.35 (2H, dt, J=5.5, 7.8 Hz, —CONH—C<u>H</u>$_2$—C—), 3.41 (6H, s, CH$_3$—N$^+$—CH$_3$), 3.99 (2H, t, J=7.8 Hz, —CH$_2$—C<u>H</u>$_2$—N$^+$—), 4.44 (2H, t, J=7 Hz, —CH$_2$—C<u>H</u>$_2$— phenyl), 4.67 (2H, s, N$^+$—CH$_2$—C=O), 7.05–7.4 (5H, m, phenyl), 7.9 (1H, t, J=5.5 Hz, —CONH—)

IR (NaCl) [cm$^{-1}$] 3700–3100, 3084 (ν CH, phenyl), 3030 (ν CH, phenyl), 2952 (ν $_{as}$CH$_3$), 2924 (ν $_{as}$CH$_2$), 2848 (ν $_s$CH$_2$), 1743 (ν C=O, ester), 1645 (ν C=O, amide), 1607 (phenyl), 1552 (δ NH, ν C—N), 1485, 1381 (δ $_s$CH$_3$), 1230, 1194 (ν C—O, ester), 1151, 1074, 1024, 960, 901, 746.

Inventive Example 12

Synthesis of N,N-dimethyl-N-(3-methyl-4-isopropylphenyl)oxycarbonylmethyl-N-(3-(octadecanoylamino)propyl)ammonium chloride A 33.18 g (0.090 mol) portion of N-octadecanoyl-N',N'-dimethyl-1,3-diaminopropane and 120 ml of chloroform were put into a flask, and 22.44 g (0.099 mol) of 3-methyl-4-isopropylphenyl chloroacetate was added thereto at 25° C. spending 5 minutes. The reaction mixture was stirred at 25° C. for 36 hours and then, after confirming disappearance of the most part of chloroacetate by $^1$H-NMR, the solvent was evaporated under a reduced pressure. The thus obtained viscous oil was dissolved in 300 ml of acetone and cooled to 5 to 10° C. to effect precipitation of a white precipitate. Thereafter, in the same manner as described in Inventive Example 1, the title compound (to be referred to as betaine ester (12) hereinafter) was obtained as a white solid. Yield 41.80 g (0.070 mol; yield 78.0%).

$^1$H-NMR (200 MHz, CDCl$_3$): δ[ppm] 0.88 (3H, t, J=6.4 Hz, —(CH$_2$)$_{16}$—C<u>H</u>$_3$), 1.21 (6H, d, J=6.8 Hz, —CH(C<u>H</u>$_3$)$_2$), 1.26 (28H, br s, —(C<u>H</u>$_2$)$_{14}$—CH$_3$), 1.5–1.7 (2H, m, —C<u>H</u>$_2$—CH$_2$—CONH—), 2.0–2.3 (2H, m, N—C—CH$_2$—C—N), 2.28 (2H, t, J=7.8 Hz, —CH$_2$—C<u>H</u>$_2$—CONH—), 2.31 (3H, s, phenyl group 3-methyl), 3.1 (1H, quint, J=6.8 Hz, —C<u>H</u>(CH$_3$)$_2$), 3.39 (2H, dt, J=5.6, 7.6 Hz, —CONH—C<u>H</u>$_2$—C—), 3.56 (6H, s, CH$_3$—N$^+$—CH$_3$), 4.14 (2H, t, J=7.6 Hz, —CH$_2$—C<u>H</u>$_2$—N$^+$—), 5.23 (2H, s, N$^+$—CH$_2$—C=O), 6.89 (1H, s, phenyl), 6.92 (1H, J=2.5, 9.8 Hz, phenyl), 7.22 (1H, d, J=8.3 Hz, phenyl), 7.88 (1H, t, J=5.6 Hz, —CONH—)

IR (NaCl) [cm$^{-1}$] 3700–3100, 3050 (ν CH, phenyl), 2956 (ν $_{as}$CH$_3$), 2920 (ν $_{as}$CH$_2$), 2850 (ν $_s$CH$_2$), 1765 (ν C=O, ester), 1650 (ν C=O, amide), 1552 (δ NH, ν C—N), 1495 (ν C=C, phenyl), 1469, 1383 (δ $_s$CH$_3$), 1363, 1240, 1126 (δ CH, phenyl), 1086, 1020 (δ CH, phenyl), 987, 901, 822, 762 (phenyl), 719 (—(CH$_2$)$_n$—).

Inventive Example 13

Synthesis of N,N-dimethyl-N-L-menthyloxycarbonylmethyl-N-(3-(octadecanoylamino)propyl)ammonium chloride A 110.00 g (0.298 mol) portion of N-octadecanoyl-N',N'-dimethyl-1,3-diaminopropane, 76.38 g (0.328 mol) of L-menthyl chloroacetate and 450 ml of acetone were put into a 1 liter capacity four neck round bottom flask, the reactants were heated under reflux for 6 hours and then disappearance of the most part of chloroacetate was confirmed by $^1$H-NMR. The reaction mixture was allowed to stand at room temperature for 12 hours and then ice-cooled to effect precipitation of white crystals. The crystals were purified by several times of repetition of a cycle in which the supernatant solvent is discarded by decantation, the remaining crystals are mixed with 30 ml of acetone and again dissolved by heating to 55° C., the solution is ice-cooled while stirring and then the thus precipitated crystals are collected by decantation. By drying under a reduced pressure using a vacuum pump, the title compound (to be referred to as betaine ester (13) hereinafter) was obtained as white crystals. Yield 114.82 g (0.191 mol; yield 64.0%).

$^1$H-NMR (200 MHz, CDCl$_3$): δ[ppm] 0.75 (3H, d, J=6.9 Hz, >CH—C<u>H</u>$_3$), 0.90–1.00 (9H, (C<u>H</u>$_3$)$_2$—CH—, C<u>H</u>$_3$—(CH$_2$)$_{19}$—), 1.00–1.20 (2H, >—CH$_2$), 1.25 (30H, br s, —(C<u>H</u>$_2$)$_{15}$—Me), 1.4–1.9 (7H, cyclic >CH$_2$, >CH, —C<u>H</u>$_2$—CH$_2$—CONH—), 1.9–2.2 (3H, >CH, N—C—CH$_2$—C—N), 2.20 (2H, t, J=10.0 Hz, —CH$_2$—C<u>H</u>$_2$—C=O), 3.36 (2H, dt, J=5.5, 7.2 Hz, —CONH—C<u>H</u>$_2$—C—), 3.50 (3H, s, C<u>H</u>$_3$—N$^+$—CH$_3$), 3.52 (3H, s, C<u>H</u>$_3$—N$^+$—CH$_3$), 4.13 (2H, dd, J=5.5 Hz, —CH$_2$—C<u>H</u>$_2$—N$^+$—), 4.43 (1H, d, N$^+$—CH$_2$—C=O, J=16 Hz), 4.62 (1H, d, N$^+$—CH$_2$—C=O, J=16 Hz), 4.82 (1H, td, J=4.5, 10.9 Hz, >C<u>H</u>—O—C=O), 8.10 (1H, t, J=5.5 Hz, —CONH—)

IR (NaCl) [cm$^{-1}$] 3700–3150, 2954 (ν $_{as}$CH$_3$), 2920 (ν $_{as}$CH$_2$), 2850 (ν $_s$CH$_2$), 1736 (ν C=O, ester), 1655 (ν C=O, amide), 1552 (δ NH, ν C—N), 1467 (δ $_{as}$CH$_3$; δ CH, —CH$_2$—), 1408 (gem-dimethyl), 1375 (gem-dimethyl), 1227, 1205 (ν C—O, ester), 1155, 1020, 955, 918, 721 ((CH$_2$)$_n$).

Inventive Example 14

Synthesis of N,N-dimethyl-N-L-menthyloxycarbonylmethyl-N-(3-(docosanoylamino)propyl)ammonium chloride A 73.51 g (0.168 mol) portion of N-docosadecanoyl-N',N'-dimethyl-1,3-diaminopropane, 46.78 g (0.201 mol) of L-menthyl chloroacetate and 200 ml of toluene were put into a 1 liter capacity four neck round bottom flask, the reactants were stirred at 80° C. for 2.5 hours and then disappearance of the most part of chloroacetate was confirmed by $^1$H-NMR. The solvent was evaporated under a reduced pressure using an evaporator, the crude product was mixed with 500 ml of acetone and dissolved by heating to 55° C., the solution was air-cooled while stirring and then the thus precipitated crystals were collected by filtration under pressure. The thus collected white crystals were again transferred into a flask and mixed with 500 ml of acetone, and the same step was repeated 6 times to remove L-menthyl chloroacetate. By drying under a reduced pressure using a vacuum pump, the title compound (to be referred to as betaine ester (14) hereinafter) was obtained as white crystals. Yield 68.3 g (0.102 mol; yield 60.7%).

$^1$H-NMR (200 MHz, CDCl$_3$): δ[ppm] 0.75 (3H, d, J=6.9 Hz, >CH—C<u>H</u>$_3$), 0.90–1.00 (9H, (C<u>H</u>$_3$)$_2$—CH—, C<u>H</u>$_3$—(CH$_2$)$_{19}$—), 1.00–1.20 (2H, >—CH$_2$), 1.25 (38H, br s, —(C<u>H</u>$_2$)$_{19}$—Me), 1.4–1.9 (7H, cyclic >CH$_2$, >CH, —C<u>H</u>$_2$—CH$_2$—CONH—), 1.9–2.2 (3H, >CH, N—C—CH$_2$—C—N), 2.20 (2H, t, J=10.0 Hz, —CH$_2$—C<u>H</u>$_2$—C=O), 3.36 (2H, dt, J=5.5, 7.2 Hz, —CONH—C<u>H</u>$_2$—C—), 3.50 (3H, s, C<u>H</u>$_3$—N$^+$—CH$_3$), 3.52 (3H, s, C<u>H</u>$_3$—N$^+$—CH$_3$), 4.13 (2H, dd, J=5.5 Hz, —CH$_2$—CH$_2$—N$^+$—), 4.43 (1H, d, N$^+$—CH$_2$—C=O, J=16 Hz), 4.62 (1H, d, N$^+$—CH$_2$—C=O, J=16 Hz), 4.82 (1H, td, J=4.5, 10.9 Hz, >CH—O—C=O), 8.10 (1H, t, J=5.5 Hz, —CONH—)

IR (NaCl) [cm$^{-1}$] 3700–3150, 2954 ($\nu_{as}$CH$_3$), 2920 ($\nu_{as}$CH$_2$), 2850 ($\nu_s$CH$_2$), 1736 ($\nu$ C=O, ester), 1655 ($\nu$ C=O, amide), 1552 ($\delta$ NH, $\nu$ C—N), 1467 ($\delta_{as}$CH$_3$; $\delta$ CH, —CH$_2$—) 1408 (gem-dimethyl), 1375 (gem-dimethyl), 1227, 1205 ($\nu$ C—O, ester), 1155, 1020, 955, 918, 721 ((CH$_2$)$_n$).

Inventive Example 15

Softening agent compositions shown in Table 1 were prepared using the following components by the following method. Sustained aroma-releasing performance of the thus obtained softening compositions was evaluated by the following method. The results are shown in Table 2.
<Formulation Components>
Component (a)

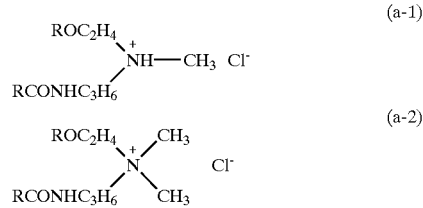

[R; Mixed straight chain alkyl groups having 17 and 15 carbon atoms (17 carbons/15 carbons (weight ratio)=60/40)]
Component (b)

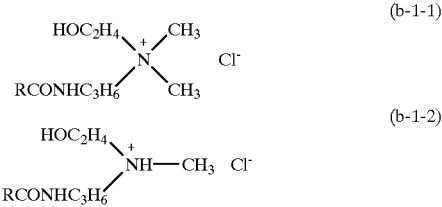

[R; As defined in the foregoing]

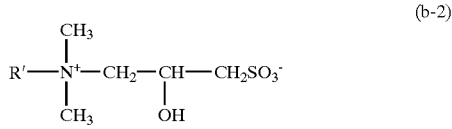

[R'; Mixed straight chain alkyl groups having 12, 14 and 16 carbon atoms (12 carbons:14 carbons:16 carbons (weight ratio)=60:25:15)]
Component (c)
 (c-1): Lunax S-50 (stearic acid, mfd. by Kao)
Component (d)
 (d-1): a product prepared by adding 21 mol in average of ethylene oxide to lauryl alcohol
Component (e);
 (e-1): calcium chloride
 (e-2) : Excel 150 (mixture of mono-, di- and tri-glyceride stearate (mo:di:tri (weight ratio)=60:35:5), mfd. by Kao)
 (e-3-1): geraniol (perfume)
 (e-3-2): 3-methyl-5-phenylpentanol (perfume)
 (e-4): 99.5% ethanol
Component (f) (Betaine Esters of the Invention)
 (f-1): betaine ester (1)
 (f-2): betaine ester (6)
<Preparation Method>

Ion exchange water was put into a beaker and heated to 60° C. The components (a) to (e) (excluding (e-4)) were added in succession while stirring, and pH was adjusted to 3.0 with N/10 hydrochloric acid. After further mixing for 30 minutes while keeping at 60° C., the mixture was cooled to 28 to 30° C. with stirring (cooling rate 1.5° C./min). After the cooling, the component (f) was dissolved in the component (e-4) and added as an ethanol solution of 40% in concentration of betaine ester. Also, when the component (b-2) was used, it was added after cooling of the addition of the component (f). Next, the mixture was heated again and, when reached to 55° C., stirred for 5 minutes and then rapidly cooled in a water bath of 5° C. After cooling to a liquid temperature of 30° C. or lower spending about 4 minutes, the water bath temperature was changed to 15° C. and, when the liquid temperature finally reached 20° C., the stirring was stopped and the mixture was allowed to stand for 1 hour.

Also, when the component (f) was not added, the same procedure was carried out except that the components (a) to (e) including (e-4) were added in succession.
<Evaluation Method of Sustained Aroma-releasing Performance>

A 0.7 g portion of each softening agent composition was added to 3 liters of tap water, a towel (100% cotton) was thoroughly soaked therein, rinsed twice in 3 liters of tap water and dried by spreading a piece of dehydrating cloth in a room of 25° C. in room temperature and 40% in relative humidity, and then changes in the aroma with the lapse of drying time was evaluated by five testers based on the following odor strength criteria. The evaluation value indicates average value of the evaluation results by five testers.

5: very strong
4: slightly strong
3: moderate
2: slightly weak
1: weak
0: no scent

TABLE 1

|  |  | Inventive product | | | | Comparative product | | |
| --- | --- | --- | --- | --- | --- | --- | --- | --- |
|  |  | 15-1 | 15-2 | 15-3 | 15-4 | 15-1 | 15-2 | 15-3 |
| Softening | a-1 | 8 |  | 8 |  | 8 |  | 8 |
| agent | a-2 |  | 15 |  | 15 |  | 15 |  |
| composition | b-1-1 | 8 |  | 8 |  | 8 |  | 8 |
| (%) | b-1-2 |  | 1 |  | 1 |  | 1 |  |
|  | b-2 |  | 1 |  | 1 |  | 1 |  |
|  | c-1 | 0.6 | 0.6 | 0.2 | 0.2 | 0.6 | 0.6 | 0.6 |
|  | d-1 | 2.5 | 2.5 | 2.5 | 2.5 | 2.5 | 2.5 | 2.5 |
|  | e-1 | 0.01 | 0.01 | 0.01 | 0.01 | 0.01 | 0.01 | 0.01 |
|  | e-2 | 0.1 | 0.1 | 0.1 | 0.1 | 0.1 | 0.1 | 0.1 |
|  | e-3-1 |  |  |  |  | 0.3 | 0.3 |  |
|  | e-3-2 |  |  |  |  |  |  | 0.3 |
|  | e-4 | 1.8 | 1.8 | 1.7 | 1.7 | 1.8 | 1.8 | 1.7 |
|  | f-1 | 1.2 | 1.2 |  |  |  |  |  |
|  | f-2 |  |  | 1.1 | 1.1 |  |  |  |
|  | water | bal. | bal. | bal. | bal. | bal. | bal. | bal. |
| Composition pH |  | 2.5 | 2.5 | 2.5 | 2.5 | 2.5 | 2.5 | 2.5 | bal: balance

TABLE 2

| Drying time | Inventive product | | | | Comparative product | | |
|---|---|---|---|---|---|---|---|
| (hr) | 15-1 | 15-2 | 15-3 | 15-4 | 15-1 | 15-2 | 15-3 |
| 0 (just after dehydration) | 0.5 | 0.5 | 0.5 | 0.5 | 1.5 | 1.5 | 0.5 |
| 1 | 1.0 | 1.0 | 1.0 | 1.0 | 1.5 | 1.5 | 1.5 |
| 2 | 1.0 | 1.0 | 1.5 | 1.5 | 1.5 | 1.5 | 1.5 |
| 3 | 1.0 | 1.0 | 1.0 | 1.0 | 0.5 | 0.5 | 0.5 |
| 17 | 1.0 | 1.0 | 0.5 | 0.5 | 0 | 0 | 0.5 |
| 24 | 1.0 | 1.0 | 0.5 | 0.5 | 0 | 0 | 0.1 |
| 72 | 1.0 | 1.0 | 0.5 | 0.5 | 0 | 0 | 0 |

Based on the results of Table 2, it was found that the betaine ester-formulated softening agent compositions of the invention have the effect to sustain scent of perfumes in comparison with the respective compositions in which only their corresponding perfumes were formulated.

Inventive Example 16

Detergent compositions for hard surface use shown in Table 3 were prepared, and detergency of soap scum stains in a bathroom bathtub and stains in a flush toilet stool, storage stability of the detergent (coloring property) and sustained release of perfumes from the bathroom bathtub were evaluated by the following methods. The results are shown in Table 3.

<Detergency of Soap Scum Stains>

Using an unwashed polypropylene bathtub which had been used under the same condition for half a year, a piece of cloth impregnated with each detergent composition was adhered to stains of the bathtub for 5 minutes and then the stains were rubbed with a sponge to evaluate removing condition of the stains visually by the following five steps. In this connection, each value shown in Table 3 is the average score of five evaluations.

5: very good washing
4: good washing
3: uneven washing
2: slight washing
1: almost no washing <Sustained Release of Aroma>

The polypropylene bathtub washed by the above method was dried at room temperature for 3 hours, and sustained release of the aroma from the bathtub surface was evaluated by five testers based on the following five step strength of aroma. The evaluation value was expressed by rounding off the fractions of the average value of the evaluation results by five testers to one decimal place.

5: very strong
4: slightly strong
3: moderate
2: slightly weak
1: weak
0: no scent <Detergency of Stains in Flush Toilet Stool>

Detergency of inorganic-organic complex stains in a flush toilet stool, which cannot be washed off by merely rubbing with a brush, was evaluated by spraying a predetermined amount of each detergent composition, rubbing the stains with a brush and then observing washed condition of the stains with the naked eye based on the following five step criteria.

⊚: good
○: slightly good
Δ: slightly bad
×: bad

<Storage Stability>

Each detergent composition was sealed in a polypropylene container and stored at 40° C. for 3 months. Appearances before and after the storage were compared and evaluated.

○: no changes in appearance
×: evident coloring compared to the appearance before storage

TABLE 3

| | Inventive product | | | | | | Comparative product | |
|---|---|---|---|---|---|---|---|---|
| | 16-1 | 16-2 | 16-3 | 16-4 | 16-5 | 16-6 | 16-1 | 16-2 |
| Detergent composition (%) | | | | | | | | |
| Betaine ester (3) | 3.5 | 3.5 | 2 | | | | | |
| Betaine ester (4) | | | | 3.5 | 3.5 | 2 | | |
| Geraniol | | | | | | | 0.9 | 1.2 |
| Octyl-benzalkonium chloride | 1.5 | 0.7 | 1.3 | 1.5 | 0.7 | 1.3 | 1.5 | 1.5 |
| Betaine compound* | 2 | 2 | 3 | 2 | 2 | 3 | 3 | 3 |
| Fatty acid alkanol amide** | 0.7 | 0.7 | 0.5 | 0.7 | 0.7 | 0.5 | 0.5 | 0.5 |
| Water*** | bal. | bal. | bal. | bal. | bal. | bal. | Bal. | bal. |
| pH (adjusted with NaOH and HCl) | 6 | 6 | 6 | 6 | 6 | 6 | 6 | 6 |
| Evaluation results | | | | | | | | |
| Detergency of soap scum stains | 5 | 5 | 4.8 | 5 | 5 | 5 | 5 | 5 |
| Sustained release of perfume from bathtub surface | 1 | 1 | 1 | 1 | 1 | 1 | 0 | 0 |
| Detergency of stains in stool | ⊚ | ⊚ | ⊚ | ⊚ | ⊚ | ⊚ | ⊚ | ⊚ |
| Storage stability (coloring) | ○ | ○ | ○ | ○ | ○ | ○ | ○ | ○ |

*N'-Lauroylaminopropyl-N,N-dimethyl-N-carboxymethylammonium betaine

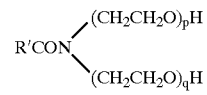

[In this formula, R' is as defined in the foregoing, p is 1.6 and q is 0.5.]

Based on the results of Table 3, it was found that the betaine ester of the invention can be formulated stably in the hard surface detergent and gradually releases the aromatic component by remaining and adhering on the hard surface after washing.

Inventive Example 17

Detergent compositions for clothing use shown in Table 4 were prepared, and their effect to inhibit the peculiar bad smell generated by indoor drying of clothes washed using these detergent compositions was comparatively evaluated by the following method. The results are shown in Table 5.

<Inhibition Effect Evaluation Method>

Cotton towels were used by ten persons for 2 weeks for wiping up their bodies soaked with sweet and water and then lightly moistened with ion exchange water, wrapped in vinyl bags and allowed to stand at 30° C. for 2 days. Thereafter, each of these cotton towels was cut in half, and 10 pieces of the one side were washed with a comparative detergent system, and 10 pieces of the other side with a test detergent system. After washing and dehydration, they were dried in the same room of 30° C. in temperature and 55% in humidity, and the strength of bad smell from the towels after 4 or 10 hours of the commencement of drying was evaluated by five testers based on the following six step criteria to calculate average value of the results. Also, a case in which the smell was felt as the aroma of perfume was evaluated as ○, and the other case of unpleasant smell as ×.

5: very strong
4: slightly strong
3: moderate
2: slightly weak
1: weak
0: no smell

TABLE 4

|  |  | Test detergent | Comparative detergent |
|---|---|---|---|
| Detergent Composition (%) | LAS *1 | 20.0 | 20.0 |
|  | Sodium palmitate | 2.0 | 2.0 |
|  | Zeolite *2 | 20.0 | 20.0 |
|  | Amorphous silicate *3 | 7.0 | 7.0 |
|  | Sodium sulfite | 2.0 | 2.0 |
|  | Sodium sulfate | 23.0 | 23.0 |
|  | Citric acid | 10.0 | 10.0 |
|  | PEG *4 | 2.0 | 2.0 |
|  | Betaine ester (1) | 1.2 | — |
|  | Geraniol | — | 0.3 |
|  | Moisture | 1.0 | 1.0 |
|  | Total | 100.0 | 100.0 |
| Shape |  | granular | granular |
| Concentration used |  | 49 g/30 L | 40 g/30 L |
| Washing solution pH |  | 8.0 | 8.0 |

*1 LAS: an alkylbenzenesulfonic acid ("Alkene L" (alkyl chain having 10 to 14 carbon atoms), mfd. by Nisseki Senzai) neutralized with 48% sodium hydroxide aqueous solution
*2 Zeolite: 4A type zeolite, average particle size 3 μm
*3 Amorphous silicate: JIS No. 2 sodium silicate
*4 PEG: polyethylene glycol, average molecular weight 8,000

TABLE 5

| Test towel | | A | B | C | D | E | F | G | H | I | J |
|---|---|---|---|---|---|---|---|---|---|---|---|
| Test detergent system (4 hr drying) | Odor strength | 0.6 | 0.6 | 0.4 | 0.6 | 0.6 | 0.8 | 0.6 | 0.6 | 0.4 | 0.6 |
|  | Odor quality | ○ | ○ | ○ | ○ | ○ | ○ | ○ | ○ | ○ | ○ |
| Test detergent system (10 hr drying) | Odor strength | 0.4 | 0.4 | 0.4 | 0.4 | 0.4 | 0.6 | 0.6 | 0.4 | 0.2 | 0.4 |
|  | Odor quality | ○ | ○ | ○ | ○ | ○ | ○ | ○ | ○ | ○ | ○ |
| Comparative detergent system (4 hr drying) | Odor strength | 1.2 | 1.0 | 1.0 | 1.6 | 1.0 | 1.6 | 1.0 | 1.0 | 1.0 | 1.0 |
|  | Odor quality | × | × | × | × | × | × | × | × | × | × |
| Comparative detergent system (10 hr drying) | Odor strength | 1.0 | 1.0 | 0.8 | 1.2 | 1.0 | 1.2 | 1.0 | 1.0 | 1.0 | 1.0 |
|  | Odor quality | × | × | × | × | × | × | × | × | × | × |

Inventive Example 18

Using the following test solutions, a fungal resistance test was carried out by the following method. The results are shown in Table 6.

<Test Solutions>

Each of betaine ester (1), betaine ester (3) and geraniol was dissolved in 99.5% ethanol to prepare solutions having the following concentrations and used as test solutions (A), (B) and (C), respectively.

Test solution (A): betaine ester (1), 1.17% in concentration

Test solution (B) betaine ester (3), 1.00% in concentration

Test solution (C): geraniol, 0.300% in concentration

<Fungal Resistance Test>

(1) Preparation of Test Cloth

A 0.3 ml portion of each test solution or 0.3 ml of 99.5% ethanol used as a control was separately coated on a cotton-polyester mixture test cloth cut into a disc of 25 mm in diameter and then the cloth was dried at 25° C. under 30% relative humidity for 48 hours to be used as a test cloth. Three sheets of the test cloth were prepared for one test solution and used in the test.

(2) Fungal Resistance Test

A plate agar medium having the following composition was prepared to a thickness of 15 mm in a Petri dish of 150 mm in diameter. The medium was used by sterilizing it in advance at 120° C. for 20 minutes in an autoclave.

Medium composition;

Pure water: 1,500 ml, glucose: 15 g, agar: 23 g, inorganic salts stock solution ($NH_4NO_3$ 90 g, $KH_2PO_4$ 60 g, $MgSO_4 \cdot 7H_2O$, 15 g, KCl 15 g, pure water 1,000 g): 50 ml Each test cloth was put on the above medium, and about 1 ml of a spore suspension prepared by dispersing spores of a fungus (*Aspergillus niger*) in sterile water (containing 0.005% sodium dioctylsulfosuccinate) was sprayed. This was cultured at 29±1° C. for 7 days to carry out comparative test of fungal resistance by inspecting growing condition of the fungus on the periphery or surface of the sample, and the results were evaluated based on the following five step criteria by observing growth condition of the fungus on the test cloth surface with the naked eye and under a microscope. That is, when the fungus is not grown on the surface of a test cloth and also, when the test cloth is peeled from the medium, the fungus is not grown on the backside but forming an inhibition zone, the result is judged as excellent in fungal resistance (NG). In this connection, when the inhibition zone was not clearly observed on the medium surface, the test cloth surface was observed with a microscope under 50×objective using an ocular micrometer to measure the area of fungal growth by millimeter unit, and the fungal resistance was evaluated based on the size of fungal growth area occupying the test cloth surface (TG, SG, MG or HG).

Completely no fungal growth: NG (no growth)

Growth on less than 10% of the surface area: TG (trace of growth)

Growth on 10% or more and less than 30% of the surface area: SG (slight growth)

Growth on 30% or more and less than 60% of the surface area: MG (moderate growth)

Growth on 60% or more of the surface area: HG (heavy growth)

TABLE 6

| Test solution | (A) | (B) | (C) | Control (ethanol) |
|---|---|---|---|---|
| Growth rate (%) | 0 | 0 | 35 | 85 |
|  | 0 | 0 | 32 | 75 |
|  | 0 | 0 | 40 | 85 |
| Average | 0 | 0 | 36 | 82 |
| Judgment | NG | NG | MG | HG |

As a result of the test, it was confirmed that the test cloth on which the betaine ester of the invention was coated has higher effect to inhibit generation of a fungus in comparison with the test cloth on which geraniol was coated and then dried.

What is claimed is:

1. A substance which is a betaine ester of a functional alcohol represented by a general formula (I)

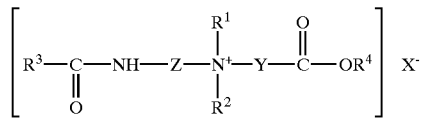

(I)

wherein each of $R^1$, $R^2$ and $R^3$ independently represents hydrogen atom or a straight- or branched-chain alkyl or alkenyl group having from 1 to 30 carbon atoms, Y represents a straight- or branched-chain alkylene group having from 1 to 4 carbon atoms, Z is a group represented by —$R^5$(OA)n— (wherein $R^5$ is a straight or branched-chain alkylene group having from 1 to 30 carbon atoms, and A is a straight- or branched-chain alkylene group having from 2 to 4 carbon atoms, and n is a number of from 0 to 10), $R^4$ represents an aromatic hydrocarbon group having from 1 to 11 carbon atoms, or an alkadienyl group, alkatrienyl group, aryl group, arylalkyl group or monocyclic, bicyclic or tricyclic terpene hydrocarbon group, each having from 12 to 30 carbon atoms, wherein a part of the hydrogen atoms on the hydrocarbon group of $R^4$ may be substituted by a halogen atom or hydroxyl group, the methylene group in the hydrocarbon group of $R^4$ may be substituted by carbonyl group, amido bond, oxygen atom or sulfur atom, the methyl group may be substituted by formyl group or —$CONH_2$, the carbon-carbon double bond may be substituted by epoxy group and, when isomers are present in $R^4$, it may be a mixture of isomers, and $X^-$ represents an anion.

2. A composition which comprises the functional alcohol releasing substance described in claim 1.

3. The composition according to claim 2, further comprising a textile conditioner or, softening agent component.

4. The composition according to claim 2, further comprising a detergent component.

5. The substance according to claim 1, wherein said betaine ester of a functional alcohol is a compound represented by a general formula (II)

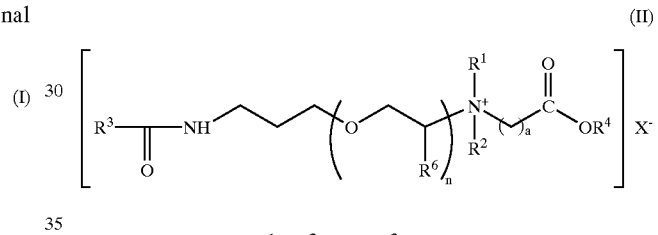

(II)

wherein each of $R^1$, $R^2$ and $R^3$ independently represents hydrogen atom or a straight- or branched-chain alkyl or alkenyl group having from 1 to 30 carbon atoms, n is a number of from 0 to 10, $X^-$ represents an anion, $R^6$ represents hydrogen atom or methyl group, and a is 1 or 2.

* * * * *